United States Patent [19]

Ochiai et al.

[11] 4,380,541
[45] Apr. 19, 1983

[54] CEPHALOSPORIN DERIVATIVES

[75] Inventors: Michihiko Ochiai, Suita; Akira Morimoto, Ikeda, both of Japan

[73] Assignee: Takeda Chemical Industries, Ltd., Osaka, Japan

[21] Appl. No.: 877,760

[22] Filed: Feb. 14, 1978

[30] Foreign Application Priority Data

Feb. 18, 1977 [JP] Japan ................... 52-17501

[51] Int. Cl.³ ............... C07D 501/20; A61K 31/545
[52] U.S. Cl. ................... 424/246; 544/22; 544/16; 544/28
[58] Field of Search .......... 544/4, 22, 26, 28, 27; 424/246

[56] References Cited

U.S. PATENT DOCUMENTS

| | | | |
|---|---|---|---|
| 3,962,227 | 6/1976 | Chauvette | 544/16 |
| 3,997,528 | 12/1976 | Yoshioka et al. | 424/246 |
| 4,007,176 | 2/1977 | Berger et al. | 424/246 |
| 4,020,058 | 4/1977 | Cocker et al. | 424/246 |
| 4,033,950 | 7/1977 | Cook et al. | 544/22 |
| 4,098,888 | 7/1978 | Ochiai et al. | 424/246 |
| 4,132,789 | 1/1979 | Nomura et al. | 424/246 |
| 4,197,298 | 4/1980 | Ochiai et al. | 424/246 |

FOREIGN PATENT DOCUMENTS

| | | |
|---|---|---|
| 852860 | 9/1977 | Belgium . |
| 2556736 | 6/1976 | Fed. Rep. of Germany . |
| 2620094 | 12/1976 | Fed. Rep. of Germany . |
| 2715385 | 11/1977 | Fed. Rep. of Germany . |

OTHER PUBLICATIONS

JACS, vol. 96 4986, (1974).
Helv Chim Acta, vol. 57 1919, (1974).
Helv Chim Acta, vol. 58 2437, (1975).

Primary Examiner—Nicholas S. Rizzo
Attorney, Agent, or Firm—Hubbell, Cohen, Stiefel & Gross

[57] ABSTRACT

Novel 7-[2-(2-aminothiazol-4-yl)-2-(syn)-methoxyiminoacetamido]cephalosporanic acid derivatives of the formula:

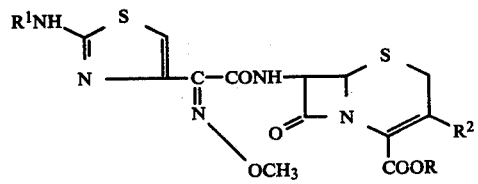

wherein $R^1NH$ is an amino group which may optionally be protected, $R^2$ is a halogen atom or a hydroxyl, thiol or amino group which may optionally be substituted; COOR is a carboxyl group which may optionally be esterified, and pharmaceutically acceptable salts thereof, have excellent antimicrobial activity against a broad spectrum of microorganisms including Gram-negative bacteria such as *Escherichia coli, Serratia marcescens, Proteus rettgeri, Enterobacter cloacae, Citrobacter freundii*. Thus, these compounds may be used as antibacterial agents for therapeutic purposes.

10 Claims, No Drawings

CEPHALOSPORIN DERIVATIVES

This invention relates to novel 7-[2-(2-aminothiazol-4-yl)-2-(syn)-methoxyiminoacetamido]cephalosporanic acids of the following formula and their salts, as well as a method for their production:

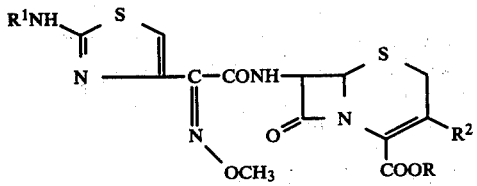

wherein $R^1NH$ is an amino group which may optionally be protected; $R^2$ is a halogen atom or a hydroxyl, thiol or amino group which may optionally be substituted; COOR is a carboxyl group which may optionally be esterified.

Intensive research undertaken by us led to the finding that reacting a compound of the formula:

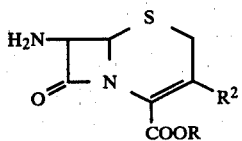

wherein R and $R^2$ are as defined hereinbefore or a salt thereof, with a compound of the formula:

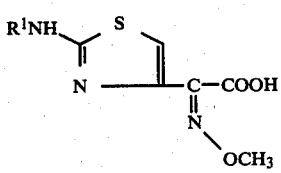

wherein $R^1$ is as defined hereinbefore, or a reactive derivative thereof, if necessary followed by removal of the protective group or groups, gives rise to a compound (I) or a salt thereof, and also that the resulting compound has excellent antimicrobial activity. This invention is based on the above findings.

Referring to the above formulas (I) and (III), $R^1NH$ is an amino group which may optionally be protected. Therefore, $R^1$ represents either a hydrogen atom or an amino-protecting group, the latter being any of the protective groups commonly employed for the protection of an amino group. Thus, for example, aromatic acyl groups such as phthaloyl, benzoyl, benzoyl substituted by halogen, nitro or lower ($C_{1-4}$) alkyl (e.g. chlorobenzoyl, p-nitrobenzoyl, p-tert-butylbenzoyl, toluoyl, etc.), naphthoyl, phenylacetyl, phenoxyacetyl, benzenesulfonyl, lower ($C_{1-4}$) alkyl-substituted benzenesulfonyl (e.g. p-tert-butylbenzenesulfonyl, toluenesulfonyl, etc.); acyl groups derived from aliphatic or halogenated aliphatic carboxylic acids such as camphorsulfonyl, methanesulfonyl, acetyl, valeryl, capryryl, n-decanoyl, acryloyl, pivaloyl, halogenoacetyl (e.g. monochloroacetyl, monobromoacetyl, dichloroacetyl, trichloroacetyl), etc.; and esterified carboxyl groups such as ethoxycarbonyl, t-butyloxycarbonyl, isobornyloxycarbonyl, phenoxycarbonyl, trichloroethoxycarbonyl, benzyloxycarbonyl, etc. $R^2$ in formulas (I) and (II) is a halogen atom (e.g. chlorine, bromine, etc.), a hydroxyl group, a thiol group or an amino group. The hydroxyl, thiol and amino groups designated by $R^2$, may each be substituted, for example by alkyl (preferably, $C_{1-4}$, e.g. methyl, ethyl, etc.), aralkyl (preferably, $C_{7-9}$, e.g. benzyl), aryl (e.g. phenyl) and other hydrocarbon groups; acyl (preferably, $C_{2-8}$, e.g. acetyl, benzoyl, etc.); or other groups. These substituent groups may further be substituted by carboxyl, sulfo, hydroxyl and so forth. When $R^2$ represents an amino group, it may form a pyrrolidino, morpholino, thiomorpholino or other group as taken together with the N atom. Thus, as examples of $R^2$, hydroxyl, methoxy, ethoxy, methylthio, carboxymethylthio, phenylthio, amino, dimethylamino, ethylamino, chlorine and bromine may be mentioned.

Referring to formulas (I) and (II), COOR is a carboxyl group which may optionally be esterified. R may for example be alkyl (e.g., methyl, ethyl, tert-butyl, tert-amyl), aralkyl (e.g., benzyl, p-nitrobenzyl, p-methoxybenzyl, trityl, benzhydryl), aryl (e.g., 1-indanyl, phthalidyl, 5-indanyl, phenyl, p-nitrophenyl), alkoxyalkyl (e.g., methoxymethyl, ethoxymethyl), acyloxyalkyl (e.g., benzyloxymethyl, phenacyl, acetoxymethyl, pivaloyloxymethyl), alkylsulfonylalkyl (e.g., $\beta$-methylsulfonylethyl), $\alpha$-alkoxycarbonyloxy-$\alpha$-alkylmethyl (e.g., $\alpha$-ethoxycarbonyloxy-$\alpha$-methylmethyl), alkylthioalkyl (e.g., methylthiomethyl), halogenoalkyl (e.g., $\beta,\beta,\beta$-trichloroethyl), trialkylsilyl (e.g., trimethylsilyl), etc.

The contemplated compound (I) of this invention is produced by reacting a compound (II) with a compound (III) or a reactive derivative thereof, if necessary followed by removal of the protective group or groups. In this process, a more satisfactory result may in some instances be obtained when the hydroxyl, thiol, amino, carboxyl or other group in the 3-substituent of compound (II) is previously protected by a procedure known per se prior to its reaction with compound (III). In such cases, the reaction should be followed by removal of the protective group or groups employed. For the above protection, the protective groups mentioned in connection with $R^1NH$ and the protective groups (such as benzyl, benzhydryl, etc.) commonly employed for the protection of hydroxyl, thiol and carboxyl may be selectively employed.

The compound (III) is used in its free form or as a reactive derivative thereof for the purpose of acylating the 7-amino group of compound (II). Thus, the compound (III) is subjected to the acylating reaction in its free form, as a salt of its carboxyl function, such as salts with alkali or alkaline earth metals (e.g. sodium, potassium, calcium, etc.) or organic amines (e.g. trimethylamine, pyridine, etc.) or a reactive derivative thereof such as acid halides (e.g. acid chloride, acid bromide, etc.), acid anhydride, mixed acid anhydrides, active amides, active esters, etc. As examples of said active esters, there may be mentioned the corresponding p-nitrophenyl ester, 2,4-dinitrophenyl ester, pentachlorophenyl ester, N-hydroxysuccinimide ester, N-hydroxyphthalimide ester, etc. As examples of said mixed acid anhydride may be mentioned the mixed anhydrides with carbonic acid monoesters such as monomethyl carbonate, monoisobutyl carbonate, etc. and the mixed anhydrides with lower alkanoic acids which may optionally be substituted by halogen, e.g. pivalic acid, trichloroacetic acid, etc. Where compound (III) is used in the form of a free acid or as a salt thereof, a suitable condensing agent is employed. As said condensing agent, there may be mentioned dehydrating agents such as N,N'-di-substituted carbodiimides (e.g. N,N'-dicyclohexylcarbodiimide, etc.), azolides (e.g. N,N'-carbonylimidazole, N,N'-thionyldiimidazole, etc.), N-ethoxycarbonyl-2-ethoxy-1,2-dihydroxyquinoline, phosphorus oxychloride, alkoxyacetylene, etc.; 2-halogenopyridinium salts (e.g. 2-chloropyridinium methyl iodide, 2-fluoropyridinium methyl iodide, etc.) and so forth. Where such a condensing agent is employed, it is likely that the reaction proceeds via the intermediate formation of a reactive derivative of compound (III). The reaction is generally conducted in a suitable solvent. The solvent may generally be selected from among halogenated hydrocarbons such as chloroform, methylene dichloride, etc., ethers such as tetrahydrofuran, dioxane, etc., dimethylformamide, dimethylacetamide, acetone or water, or a mixture thereof. The compound (III) is used generally in a proportion of about 1 to several mol. equivalents to the compound (II). The reaction is generally carried out at temperatures in the range of about −50° to +40° C. After the acylation reaction, the protective group or groups may be removed if necessary. Removal of the amino-protecting group may generally be accomplished by the methods known per se, such as the method described in Japanese Published unexamined patent application No. 52083/1975 and Pure and Applied Chemistry 7, 335 (1963) or methods analogous thereto. The resultant compound (I) may be isolated and purified by procedures known per se, such as column chromatography, extraction, precipitation, recrystallization, etc. The resultant compound (I) may be converted to a desired salt, ester or the like by procedures also known per se.

The starting compound (II) for this invention is produced by the methods disclosed in the patent literature such as Japanese Published unexamined patent applications No. 129590/1975, No. 95485/1975, No. 110593/1976, No. 138697/1976 and No. 108087/1976, German Patent No. 2458746, No. 2537974, No. 2555858 and No. 2606192, and U.S. Pat. No. 3,962,227, the methods described in scientific journals such as J.A.C.S. 96, 4986(1974), Helv. Chim. Acta 57, 1919(1974), Helv. Chim. Acta 58, 2437(1975), etc. or by methods analogous to those described methods. The 2-(2-aminothiazol-4-yl)-2-methoxyiminoacetic acid (syn-isomer)-derivative (III) can be produced, for example by the several methods described hereinafter.

[1] Reaction of a 4-halogeno-3-oxo-2-oxyiminobutyric acid derivative of formula (IV):

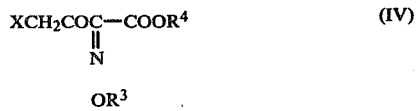

wherein X is a halogen atom such as chlorine or bromine; $R^3$ is hydrogen or methyl; $R^4$ is a lower alkyl of 1 to 3 carbon atoms such as methyl, ethyl, propyl, etc., with thiourea yields a 2-(2-aminothiazol-4-yl)-2-oxyiminoacetic acid derivative of formula (V)

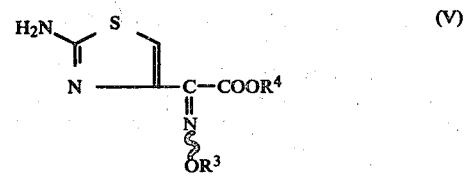

wherein $R^3$ and $R^4$ are as defined hereinbefore.

Irrespective of whether $R^3$ is hydrogen or methyl, the compound (V) is generally obtained as a mixture of syn- and anti-isomers. This reaction is generally carried out by permitting the compound (IV) to interact with thiourea in an organic solvent such as ethanol, methanol or tetrahydrofuran, either at room temperature or at an elevated temperature. The desired syn-compound can be separated and recovered from such a mixture of syn- and anti-compounds (V) by separation procedures utilizing the difference in crystallizability, solubility or other behaviors of the two isomers, of compound (V) as such, a hydrogen halide salt thereof (HBr, HCl and other salts) or a derivative thereof which is obtainable by introducing a protective group (e.g. monochloroacetyl, dichloroacethyl, etc.) into the 2-amino group, by partition chromatography or by a method such that, in the hydrolysis of the ester moiety of compound (V) or a compound having a protective group introduced into the 2-amino group of (V), the difference in the rates of hydrolysis of the syn- and anti-isomers are utilized to obtain the syn-isomer selectively. In the latter method, the rate of hydrolysis of the anti-isomer is higher than that of the syn-isomer, thus permitting removable of the anti-isomer by selective hydrolysis. The reaction for the hydrolytic cleavage of the ester linkage of compound (V) or a compound having a substituted amino group in the 2-position of the thiazole ring of (V) is generally conducted in the presence of one to several equivalents of an alkali metal hydroxide such as potassium hydroxide, sodium hydroxide or the like at a temperature from under ice-cooling to room temperature in a mixture of water and water-miscible organic solvent such as methanol, ethanol, acetone, tetrahydrofuran, dioxane, N,N-dimethylformamide, N,N-dimethylacetamide, etc. The compound (V) where $R^3$ is hydrogen, the separated syn-isomer may be methylated to the compound where $R^3$ is methyl. This methylation reaction is generally conducted in a solvent under ice-cooling to near room temperature and, in many cases, goes to completion within a few minutes to several hours. The solvent may be any solvent that will not interfere with the reaction, such as tetrahydrofuran, dioxane, methanol, ethanol, chloroform, methylene dichloride, ethyl acetate, butyl acetate, N,N-dimethylformamide, N,N-dimethylacetamide, water or the like or a mixture of such solvents. As examples of the methylating agent may be mentioned methyl halides such as methyl iodide, methyl bromide, etc., dimethyl sulfate, diazomethane, etc. Excepting the case in which diazomethane is employed, the compound (V) where $R^3$ is hydrogen is reacted with the above-mentioned methylating agent in the presence of a base such as an alkali metal carbonate (such as sodium carbonate, potassium carbonate, etc.) or an alkali metal hydroxide (such as sodium hydroxide, potassium hydroxide, etc.). In Table 1, some of the physical constants of the syn-forms of compounds (III) thus obtained are compared with those of the corresponding anti-forms.

TABLE 1

| STRUCTURE | | NMR Spectrum(ppm) | m.p. (°C.) |
|---|---|---|---|
| syn | H₂N-C(S)-N=C(NH)-CH=C(COOC₂H₅)-N=N-OH | In δ₆-DMSO 6.80s(5-H)11.6s(OH) | 185.5 |
| anti | H₂N-C(S)-N=C(NH)-CH=C(COOC₂H₅)-N(OH)= | In δ₆-DMSO 7.50s(5-H)12.5s(OH) | 145.3 |
| syn | H₂N-C(S)-N=C(NH)-CH=C(COOC₂H₅)-N=N-OCH₃ (−COOCH₃) | In CDCl₃ 6.74s(5-H)4.02s(OCH₃) (6.74s) (4.02s) | 163–164 |
| anti | H₂N-C(S)-N=C(NH)-CH=C(COOC₂H₅)-N(OCH₃)= (−COOCH₃) | In CDCl₃ 7.43s(5-H)4.07s(OCH₃) (7.48s) (4.06s) | 114–115 |
| syn | ClCH₂CONH-C(S)-N=C(NH)-CH=C(COOC₂H₅)-N=N-OCH₃ (−COOCH₃) | In CDCl₃ 7.15s(5-H)4.00s(OCH₃) (7.24s) (4.02s) | 111–112 |
| anti | ClCH₂CONH-C(S)-N=C(NH)-CH=C(COOC₂H₅)-N(OCH₃)= (−COOCH₃) | In CDCl₃ 7.94s(5-H)4.10s(OCH₃) (8.02s) (4.12s) | 81–82 |
| syn | ClCH₂CONH-C(S)-N=C(NH)-CH=C(COOH)-N=N-OCH₃ | In δ₆-DMSO 7.57s(5-H)3.95s(OCH₃) | 170–171 |
| anti | ClCH₂CONH-C(S)-N=C(NH)-CH=C(COOH)-N(OCH₃)= | In δ₆-DMSO 8.00s(5-H)4.00s(OCH₃) | 182–183 |

Note:
s; singlet
(—COOCH₃); methyl ester of the corresponding compound
In the column of NMR Spectrum, physical constants of the methyl esters are in parentheses.

[2] In the following, a process for selective production of compound (III) (syn-isomer) is described. As mentioned hereinbefore, the reaction of compound (IV) with thiourea to produce compound (V) yields a mixture of syn- and anti-isomers (with the anti-isomer predominating), but our study of conditions of this condensing cyclization reaction led to the finding of conditions under which the desired syn-isomer can be selectively produced. When the reaction of compound (IV)

with thiourea to produce compound (V) is conducted under the conditions described hereinabove, the syn- and anti-isomers are generally obtained in a ratio of 2:98 to 50:50. In contrast, the syn-isomer is selectively obtained (generally about 85:15-100:0) if this cyclization reaction is conducted in a mixture of water with a water-miscible solvent such as methanol, ethanol, acetone, tetrahydrofuran, dioxane, N,N-dimethylformamide, N,N-dimethylacetamide, N-methylpiperidone, etc. and in the presence of a basic agent. As the basic agent useful for this purpose, there may be mentioned alkali or alkaline earth metal salts of lower aliphatic carboxylic acids and inorganic or organic bases with pK values of no less than 9.5, preferably in the range of 9.8 to 12.0. As examples of said lower aliphatic carboxylic acid salt, there may be mentioned salts of lower ($C_{1-6}$) aliphatic carboxylic acids such as sodium acetate, potassium acetate, calcium acetate, barium acetate, sodium formate, sodium propionate, potassium hexanoate, etc.; as examples of said inorganic base, there may be mentioned alkali metal salts of carbonic acid such as sodium carbonate, potassium carbonate, etc.; and as examples of said organic base, there may be mentioned lower ($C_{1-4}$) alkyl-tri-substituted amines such as trimethylamine, triethylamine, tributylamine, etc. and five- to six-membered cyclic amines N-substituted by lower ($C_{1-2}$) alkyls, such as N-methylpyrrolidine, N-ethylpyrrolidine, N-mehylpiperazine, N-ethylpiperazine, etc. Where said N,N-dimethylformamide, N,N-dimethylacetamide or N-methylpyrrolidone is employed as the solvent, said basic agent need not necessarily be additionally present.

[3] The compound (V) (syn-isomer) can also be selectively produced by the following process. The research undertaken by us into a further process for selective production of the syn-isomer resulted in the finding that the syn-form of the methoxyimino compound can be selectively obtained by reacting an 2-aminothiazol-4-ylglyoxylic acid derivative of the formula:

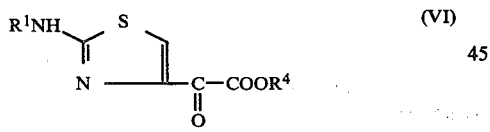

(VI)

wherein $R^1$ and $R^4$ are as defined hereinbefore, with O-methylhydroxylamine. Generally this reaction may be conducted smoothly in a suitable solvent at pH about 4.0 to about 9.0. The solvent may be any solvent that will not interfere with the reaction. Thus, for example, ethers such as ethyl ether, tetrahydrofuran, dioxane, etc.; lower alcohols such as methanol, ethanol, etc.; halogenated hydrocarbons such as chloroform, methylene dichloride, etc.; esters such as ethyl acetate, butyl acetate, etc.; water, and mixtures thereof may be mentioned. The reaction proceeds in the neighborhood of room temperature, and may be accelerated by heating, if necessary.

The starting compound (VI) for this reaction is a novel compound which has not been hitherto described in the literature, and can be produced by way of the following reaction. Thus, hydrolysis of a nitrone compound of formula (VII):

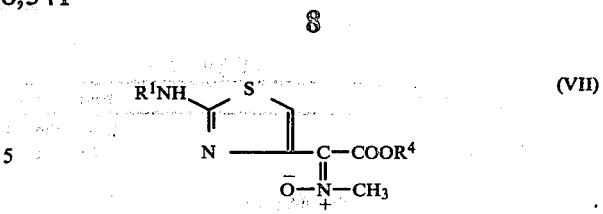

(VII)

wherein $R^1$ and $R^4$ are as defined hereinbefore, yields the compound (VI). This hydrolysis reaction is smoothly caused to proceed by mineral acid and is generally conducted in a solvent. The mineral acid may for example be hydrogen chloride, sulfuric acid or phosphoric acid. The solvent may be any solvent that will not interfere with the reaction. Thus, ethers such as tetrahydrofuran, dioxane, etc.; alcohols such as methanol, ethanol, etc.; ketones such as acetone, methyl ethyl ketone, etc.; water; etc., as well as mixtures thereof may be mentioned by way of example. The reaction may generally be conducted under ice-cooling to room temperature conditions. The starting compound V(II) is a novel compound which has never been described in the literature and can be produced by methylating the compound of general formula (V) wherein $R^3$ is hydrogen or a compound having a protective group introduced into 2-amino moiety of the thiazole ring of (V). The conditions of this methylation reaction are essentially the same as those used for the methylation of compound (V) wherein $R^3$ is hydrogen. Under these conditions of methylation, whereas the syn-form of compound (V) (where $R^3=H$) substantially does not give this nitrone compound (VII), the methylation of the anti-isomer ($R^3=H$) yields the nitrone compound (VII) preferentially. The compound of general formula (IV) can be produced, for example by the methods described in J. Med. Chem. 16, 978 (1973), Helv. Chim. Acta. 49, 26(1966), J. Am. Chem. Soc. 60, 1328(1938) and German DOS 2556736 as well as by methods analogous thereto.

The compound obtained by the above procedure, which has the formula:

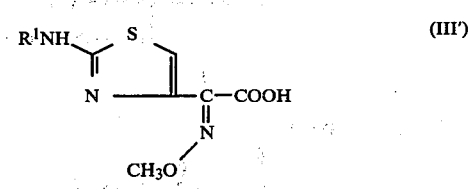

(III')

wherein R' is as defined hereinbefore, or a reactive derivative thereof, is reacted with compound (II) as is the case with compound (II), if necessary followed by removal of the protective group or groups, to obtain a compound of the formula:

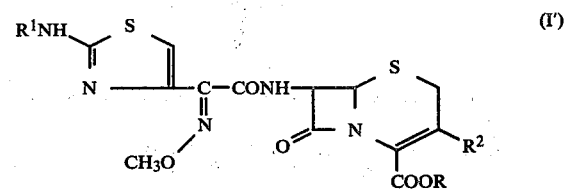

(I')

wherein R, R' and $R^2$ are as defined hereinbefore. This compound (I') has excellent antimicrobial activity.

The cephalosporin derivative of formula (I) thus obtained is considered to have tautomeric structures of the following 2-aminothiazole and 2-iminothiazoline forms:

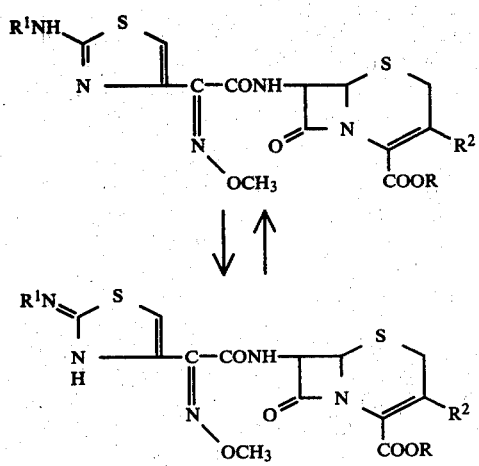

However, the thiazole form is used throughout this specification. The compound of formula (I) may be used either in its free form or as any of salts pharmacologically and pharmaceutically acceptable in the field of cephalosporins and penicillins in general. For example, the 4-carboxyl group may form a salt, e.g. with a non-toxic alkali metal cation such as sodium or potassium, a basic amino acid such as arginine, ornithine, lysine, histidine or the like, a polyhydroxyalkylamine such as N-methylglucamine, diethanolamine, triethanolamine, trishydroxymethylaminomethane or the like. The amino or imino group in the 3-substituent or/and 7-substituent may also form a salt, e.g. with a mineral acid such as hydrochloric acid, sulfuric acid, hydrobromic acid or nitric acid or an organic acid such as maleic acid or oxalic acid. The above carboxyl group may also be a biologically active ester derivative which will for example be conducive to an increased blood level and prolonged efficacy. As ester residues effective for such purposes, there may be employed lower alkoxymethyl groups such as methoxymethyl, ethoxymethyl isopropoxymethyl, α-methoxyethyl, α-ethoxyethyl, etc.; α-lower alkoxy-α-substituted methyl groups such as α-lower alkoxyethyl, etc.; lower ($C_{1-3}$) alkylthiomethyl groups such as methylthiomethyl, ethylthiomethyl, isopropylthiomethyl, etc.; acyloxymethyl groups such as pivaloyloxymethyl, α-acetoxybutyl, etc.; α-acyloxy-α-substituted methyl groups such as ethoxycarbonyloxy-1-methylmethyl; indan-5-yl; phthalidyl; etc. The salts and esters of these compounds (I) are also encompassed by compound (I).

Like the known cephalosporin or penicillin drugs, the compound (I) of this invention is administered orally or by other routes in such dosage forms as injections, capsules, powders, granules and tablets as formulated by conventional procedures. The carriers which may be employed in the formulation of injectable solutions include distilled water, physiological saline, etc. Regarding said capsules, powders, granules and tablets, compound (I) is used in admixture with pharmaceutically acceptable known excipients (e.g. starch, lactose, saccharum album, calcium carbonate, calcium phosphate, etc.), binders (e.g. starch, gum Arabic, carboxymethyl-cellulose, hydroxypropyl-cellulose, crystalline cellulose, etc.), lubricants (e.g. magnesium stearate, talc, etc.) and disintegrators (e.g. carboxymethylcalcium, talc, etc.). Thus, compounds (I) are safe, less toxic and novel compounds having excellent antimicrobial activity against a broad spectrum of microorganisms including Gram-negative bacteria such as *Escherichia coli, Serratia marcescens, Proteus rettgeri, Enterobacter cloacae, Citrobacter freundii*, etc., are resistant to β-lactamase. The compounds (I) can be used, for example as disinfectants for removing said microorganisms from surgical instruments and as drugs for the treatment of infectious diseases. When, among compounds (I),7-[2-(2-aminothiazol-4-yl)-2-(syn)-methoxyiminoacetamido]-3-methoxy-3-cephem-4-carboxylic acid sodium salt or pivaloyloxymethyl ester; sodium 7-[2-(2-aminothiazol-4-yl)-2-(syn)-methoxyiminoacetamido]-3-methylthio-3-cephem-4-carboxylate; or 7-[2-(2-aminothiazol-4-yl)-2-(syn)-methoxyiminoacetamido]-3-chloro-3-chphem-4-carboxylic acid sodium salt or pivaloyloxymethyl ester, for instance, is employed as a drug in the treatment of infectious diseases, for example in the treatment of the intraperitoneal, respiratory organ, urinary tract or/and other infections caused by any of said microorganisms, the compound (I) may be safely administered to mammals including man, mouse and rat at a daily dose level ranging from 0.5 to 80 mg, preferably from 1 to 20 mg per kilogram of body weight in 3 to 4 installments a day.

EXAMPLE 1

In 5 ml of methylene chloride were suspended 277 mg of 2-(2-chloroacetamidothiazol-4-yl)-2-(syn)-methoxyiminoacetic acid, which were then dissolved by the addition of 120 mg of triethylamine. To this solution were added 208 mg of phosphorus pentachloride and, after stirring for 20 minutes at room temperature, 20 ml of n-hexane were added. The resultant oily fraction is separated by decantation and dissolved in 10 ml of tetrahydrofuran. Thus was obtained a solution of 2-(2chloroacetamidothiazol-4-yl)-2-(syn)-methoxyiminoacetyl chloride.

On the other hand, 230 mg of 7-amino-3-methoxy-3-cephem-4-carboxylic acid were dissolved in 10 ml of 50% aqueous tetrahydrofuran containing 242 mg of triethylamine and while the solution was stirred under ice-cooling, the above solution of acid chloride in tetrahydrofuran was added dropwise. The reaction mixture was poured into water, adjusted to pH 2.0 with 1 N-hydrochloric acid and extracted with ethyl acetate. The ethyl acetate layer was washed with water, dried over magnesium sulfate and distilled to remove the ethyl acetate. Finally, ether was added to the residue, whereby crude 7-[2-(2-chloroacetamidothiazol-4-yl)-2-(syn)-methoxyiminoacetamido]-3-methoxy-3-cephem-4-carboxylic acid was obtained as crystalline powders. 200 mg.

NMR spectrum (60 MHz, in $d_6$-DMSO): 3.60 ppm(2H, singlet, 2-CH$_2$), 3.75, 3.89 ppm(6H, 2 singlet, OCH$_3$x2), 4.33 ppm (2H, singlet, ClCH$_2$CO), 5.13 ppm(1H, d, 6-H), 5.59 ppm (1H, doublet of doublet, 7-H); 7.47 ppm(1H, singlet, thiazole-5H)

In 3 ml of N,N-dimethylacetamide were dissolved 150 mg of the above product. After the addition of 50 mg of thiourea, the solution was stirred at room temperature for 14 hours. Ether was added to the reaction mixture and the supernatant is discarded by decantation. The remaining oil was suspended in water and the mixture was adjusted to pH 7 with sodium hydrogen carbonate and filtered to remove the insolubles. The filtrate was purified by passing through a column of Amberlite XAD-2(produced by Rohm & Haas Co. Ltd.). By the above procedure were obtained 95 mg of sodium 7-[2-(2-aminothiazol-4-yl)-2-(syn)-methoxyiminoacetamido]-3-methoxy-3-cephem-4-carboxylate as white powders.

Elemental analysis, for $C_{14}H_{14}N_5O_6S_2Na.2.5H_2O$: Calcd. C, 34.99; H, 3.99; N, 14.58; Found C, 35.18; H, 3.66; N, 14.28

NMR spectrum (60 MHz, in $D_2O$): 3.60 ppm(2H, quartet, 2-$CH_2$), 3.76(3H, singlet, 3-$OCH_3$), 4.01 ppm(3H, singlet, =$NOCH_3$) 5.24 ppm(1H, doublet, 6-H), 5.66 ppm(1H, doublet, 7-H), 7.06 ppm(1H, singlet, thiazol-5H)

EXAMPLE 2

A tetrahydrofuran solution (5 ml) prepared from 277 mg of 2-(2-chloroacetamidothiazol-4-yl)-2-(syn)-methoxyiminoacetic acid as in Example 1 was added to 7 ml of 50% aqueous tetrahydrofuran containing 245 mg of 7-amino-3-methylthio-3-cephem-4-carboxylic acid and 220 mg of triethylamine, dropwise under ice-cooling and stirring. The mixture was stirred for 2 hours, after which it was poured into water. The mixture is adjusted to pH 2 by the addition of 1 N-hydrochloric acid and extracted with ethyl acetate. The organic layer was washed with water, dried and concentrated to obtain a crude 7-[2-(2-chloroacetamidothiazol-4-yl)-2-(syn)-methoxyiminoacetamido]-3-methylthio-3-cephem-4-carboxylic acid. 240 mg The above product was dissolved in 1 ml of N,N-dimethylacetamide and, after the addition of 150 mg of thiourea, the solution was stirred at room temperature for 15 hours. The reaction mixture was poured into ether and the resultant precipitate was collected, dissolved in a 5% aqueous solution of sodium hydrogen carbonate and purified by passing through a column of Amberlite XAD-2. By the above procedure was obtained sodium 7-[2-(2-aminothiazol-4-yl)-2-(syn)-methoxyiminoacetamido]-3-methylthio-3-cephem-4-carboxylate as white powders. 30 mg.

NMR spectrum (60 MHz, in $D_2O$): 2.10 ppm(3H, singlet, $SCH_3$), 3.62 ppm(2H, quartet, 2-$CH_2$), 3.95 ppm(3H, singlet, =N—$OCH_3$), 5.10 ppm(1H, doublet, 6-H), 5.71 ppm(1H, doublet, 7-H), 7.10 ppm(1H, singlet, thiazole-5H)

EXAMPLE 3

As in Examples 1 and 2, the acid chloride prepared from 277 mg of 2-(2-chloroacetamidothiazol-4-yl)-2-(syn)-methoxyiminoacetic acid was reacted with 233 mg of 7-amino-3-chloro-3-cephem-4-carboxylic acid and, thereafter, the reaction product was treated as described. By this procedure were obtained 20 mg of sodium 7-[2-(2-aminothiazol-4-yl)-2-(syn)-methoxyiminoacetamido]-3-chloro-3-cephem-4-carboxylate in white powdery form.

NMR spectrum (60 MHz, in $D_2O$): 3.60 ppm(2H, quartet, 2-$CH_2$), 3.90 ppm(3H, singlet, =$NOCH_3$), 5.20 ppm(1H, doublet, 6-H), 5.71 ppm(1H, doublet, 7-H), 7.04 ppm(1H, singlet, thiazole-5H)

EXAMPLE 4

In 5 ml of N,N-dimethylformamide was dissolved 480 mg of sodium 7-[2-(2-aminothiazol-4-yl)-2-(syn)-methoxyiminoacetamido]-3-methoxy-3-cephem-4-carboxylate (2.5 hydrate): Under ice-cooling and stirring, 363 mg of iodomethyl pivalate were added. The reaction was carried out under stirring for 15 minutes and 20 ml of ethyl acetate were poured into the reaction mixture. The mixture was washed with water, a 3% aqueous solution of sodium hydrogen carbonate and a saturated aqueous solution of sodium chloride in the order mentioned and dried over magnesium sulfate. The ethyl acetate was distilled off and the resultant frothy residue was dissolved in a small amount of ethyl acetate. The solution was filtered and, following addition of ether, the filtrate was cooled in a refrigerator overnight. Finally, the precipitate was collected by filtration. By the above procedure were obtained 200 mg of pivaloyloxymethyl 7-[2-(2-aminothiazol-4-yl)-2-(syn)-methoxyiminoacetamido]-3-methoxy-3-cephem-4-carboxylate in powdery form.

NMR spectrum (60 MHz, in $CDCl_3$): 1.24 ppm(9H, singlet, t-$C_4H_9$), 3.40 ppm(2H, singlet, 2-$CH_2$), 3.82 ppm(3H, singlet, 3-$OCH_3$), 4.08 ppm(3H, singlet, =$NOCH_3$), 5.12 ppm(1H, doublet, 6-H), 5.71 ppm(1H, doublet of doublet, 7-H), 5.94 ppm(2H, singlet, —$OCH_2O$—), 6.86 ppm(1H, singlet, thiazole-5H)

EXAMPLE 5

In 5 ml of N,N-dimethylformamide were dissolved 439 mg of sodium 7-[2-(2-aminothiazol-4-yl)-2-(syn)-methoxyiminoacetamido]-3-chloro-3-cephem-4-carboxylate(dihydrate) and, under ice-cooling and stirring, 363 mg of iodomethyl pivalate were added. After being stirred for 15 minutes, the mixture was worked up as in Example 4 to obtain 185 mg of pivaloyloxymethyl 7-[2-(2-aminothiazol-4-yl)-2-(syn)-methoxyiminoacetamido]-3-chloro-3-cephem-4-carboxylate in powdery form.

NMR spectrum (60 MHz, in $CDCl_3$): 1.22 ppm(9H, singlet, t-$C_4H_9$), 3.60 ppm(2H, quartet, 2-$CH_2$), 4.10 ppm(3H, singlet, =$NOCH_3$), 5.10 ppm(1H, doublet, 6-H), 5.81 ppm(1H, doublet of doublet, 7-H), 5.94 ppm(2H, singlet, —$OCH_2O$—), 6.84 ppm (1H, singlet, thiazole-5H).

REFERENCE EXAMPLE 1

To 200 ml of water were added 38 g of sodium nitrite together with 53 g of methyl acetoacetate. Under ice-cooling and stirring, 200 ml of 4 N-sulfuric acid were added dropwise over a period of about 1 hour. During this period, the temperature of the reaction mixture was maintained at 5°–8° C. The mixture was further stirred within this temperature range for 2.5 hours. Then, it was extracted twice with 300 ml portions of ethyl acetate and the extracts are combined and washed twice with a standard aqueous solution of sodium chloride. Then, a solution of 96.9 g of sodium carbonate in 1 l of water was divided into three portions and the methyl 3-oxo-2-hydroxyiminobutyrate was extracted from the ethyl acetate layer previously obtained (3 times). To the water layer (1 l) were added 200 ml of methanol and, under ice-cooling and stirring, 150 g of dimethyl sulfate were added dropwise over a period of 10 minutes. After the dropwise addition was completed, the mixture was stirred at room temperature for 1.5 hours. It was then extracted twice with 300 ml of ethyl acetate, washed with water and dried. The ethyl acetate layer was distilled off and the residue is cooled with ice, whereupon it solidified. This solid was collected by filtration and rinsed with a small amount of water. By this procedure was obtained methyl 3-oxo-2-methoxyiminobutyrate as white crystals. 52.3 g; m.p. 64.4° C.

Elemental analysis, for $C_6H_9NO_4$; Calcd. C, 45.28; H, 5.70; N, 8.80; Found C, 44.93; H, 5.61; N, 8.71

NMR spectrum (60 MHz, in CDCl₃): 2.40 ppm(3H, singlet $$-\underset{\underset{O}{\|}}{C}-CH_3),$$

3.86 ppm(3H, singlet, COOCH₃), 4.10 ppm(3H, singlet, =NOCH₃)

REFERENCE EXAMPLE 2

In 150 ml of chloroform were dissolved 40 g of methyl 3-oxo-2-methoxyiminobutyrate. The solution was warmed to 40° C. and a solution of 40 g of bromine in 50 ml of chloroform was added dropwise over a period of one hour. Then, the reaction was conducted at room temperature with stirring for one hour. The reaction mixture was washed with a 5% aqueous solution of sodium hydrogen carbonate and water in that order and the organic layer was dried. The solvent was then distilled off under reduced pressure to obtain methyl 4-bromo-3-oxo-2-methoxy-iminobutyrate as an oil. 52.1 g NMR spectrum (60 MHz, in CDCl₃): 3.82 ppm(3H, singlet, COOCH₃), 4.09 ppm(3H, singlet, =N—OCH₃), 4.27 ppm(2H, singlet, BrCH₂CO)

In 350 ml of tetrahydrofuran were dissolved 52 g of methyl 4-bromo-3-oxo-2-methoxyiminobutyrate, followed by addition of 250 ml of water. Then, 89.1 g of sodium acetate trihydrate and 33.2 g of thiourea were added. The reaction was carried out at room temperature with stirring for 18 hours. To the reaction mixture were added 200 ml of a 5% aqueous solution of sodium hydrogen carbonate, followed by extraction with ethyl acetate. The organic layer was washed with water and dried. The solvent was distilled off under reduced pressure and 200 ml of ether were added to the residue. The resultant crystals were collected by filtration, whereby methyl 2-(2-aminothiazol-4-yl)-2-(syn)-methoxyiminoacetate was obtained as crystals. 24.8 g; m.p. 164.9° C.

Elemental analysis, for C₇H₉N₃O₃S: Calcd. C, 39.06; H, 4.21; N, 19.52; Found C, 38.78; H, 4.15; N, 19.33

NMR spectrum (60 MHz, in CDCl₃): 3.84 ppm(3H, singlet, COOH₃), 4.02 ppm(3H, singlet, =NOCH₃), 5.74 ppm(2H, broad singlet, NH₂), 6.74 ppm(1H, singlet, thiazole-5H)

REFERENCE EXAMPLE 3

In 90 ml of N,N-dimethylacetamide were dissolved 21.5 g of methyl 2-(2-aminothiazol-4-yl)-2-(syn)-methoxyiminoacetate and, under ice-cooling, 13.6 g of chloroacetyl chloride were added dropwise. The mixture was stirred under ice-cooling for 30 minutes and, then, at room temperature for 30 minutes. After the addition of 500 ml of water, the mixture was extracted twice with ethyl acetate. The extract was washed with a 5% aqueous solution of sodium hydrogen carbonate and water in the order mentioned and dried. Finally the solvent was distilled off to obtain crystals of methyl 2-(2-chloroacetamidothiazol-4-yl)-2-(syn)-methoxyiminoacetate. 25 g; m.p. 130.8° C.

Elemental analysis, for C₉H₁₁N₃O₄SCl: Calcd. C, 37.05; H, 3.45; N, 14.40; Found C, 37.30; H, 3.40; N, 14.35

NMR spectrum (60 MHz, in CDCl₃): 3.90 ppm(3H, singlet, COOCH₃), 4.02 ppm(3H, singlet, =NOCH₃), 4.26 ppm(2H, singlet, ClCH₂CO), 7.24 ppm(1H, singlet, thiazole-5H).

REFERENCE EXAMPLE 4

To a solution of 19.2 g of potassium hydroxide in a mixture of 170 ml water and 900 ml ethanol, there were added 20 g of methyl 2-(2-chloroacetamidothiazol-4-yl)-2-(syn)-methoxyiminoacetate. The mixture was stirred at room temperature for 2 hours. The ethanol was distilled off under reduced pressure and, after 170 ml of water were added, the residue was washed with 200 ml of ethyl acetate. The water layer was adjusted to pH 2 with 10% hydrochloric acid and extracted twice with 300 ml of ethyl acetate. The extracts were combined, washed with a saturated aqueous solution of sodium chloride and dried. The solvent was distilled off to obtain crystals of 2-(2-chloroacetamidothiazol-4-yl)-2-(syn)-methoxyiminoacetic acid. 16.8 g; m.p. 170°-171° C.

Elemental analysis, for C₈H₈N₃O₄SCl: Calcd. C, 34.60; H, 2.90; N, 15.13; Found C, 34.97; H, 3.03; N, 14.74

NMR spectrum (60 MHz, in d₆-DMSO); 3.95 ppm(3H, singlet, =NOCH₃), 4.40 ppm(2H, singlet, ClCH₂CO), 7.57 ppm(1H, singlet, thiazole-5H)

What we claim is:

1. A compound of the formula:

$$R^1NH-\overset{S}{\underset{N}{\|}}-\underset{\underset{OCH_3}{\|}}{C}-CONH-\overset{}{\underset{O}{\|}}\overset{S}{\underset{N}{\|}}R^2$$
$$COOR$$

wherein R¹ is hydrogen; R² is chloro, methoxy or methylthio and R is hydrogen or pivaloyloxymethyl and pharmacologically and pharmaceutically acceptable salts thereof.

2. A compound as claimed in claim 1, wherein the pharmacologically and pharmaceutically acceptable salt is a nontoxic alkali metal cation salt, a basic amino acid salt, a polyhydroxyalkylamino salt selected from the group consisting of N-methylglucamine, diethanolamine, triethanolamine and trishydroxymethylaminomethane, a mineral acid salt or an organic acid salt.

3. A compound as claimed in claim 1, which is 7-[2-(2-aminothiazol-4-yl)-2-(syn)-methoxyiminoacetamido]-3-methoxy-3-cephem-4-carboxylic acid.

4. A compound as claimed in claim 1, which is 7-[2-(2-aminothiazol-4-yl)-2-(syn)-methoxyiminoacetamido]-3-methylthio-3-cephem-4-carboxylic acid.

5. A compound as claimed in claim 1, which is 7-[2-(2-aminothiazol-4-yl)-2-(syn)-methoxyiminoacetamido]-3-chloro-3-cephem-4-carboxylic acid.

6. A compound as claimed in claim 1, which is pivaloyloxymethyl 7-[2-(2-aminothiazol-4-yl)-2-(syn)-methoxyiminoacetamido]-3-methoxy-3-cephem-4-carboxylate.

7. A compound as claimed in claim 1, which is pivaloyloxymethyl 7-[2-(2-aminothiazol-4-yl)-2-(syn)-methoxyiminoacetamido]-3-chloro-3-cephem-4-carboxylate.

8. A pharmaceutical composition which contains an antibacterially effective amount of a compound as claimed in claim 1, together with a pharmaceutically acceptable carrier or carriers therefor, said composition being administrable in a unit dosage form.

9. A method for the treatment of diseases caused by bacteria, which comprises internally administering to a mammal a pharmaceutically effective amount of a compound as claimed in claim 1.

10. A compound of the formula

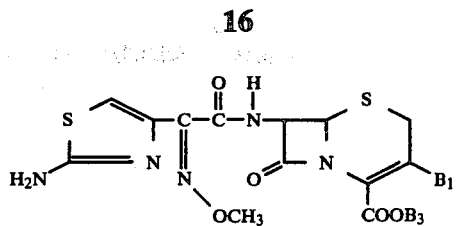

wherein $B_1$ is selected from the group consisting of chloro, methoxy or alkylthio of 1 to 4 carbon atoms; $B_3$ is selected from the group hydrogen, pharmaceutically acceptable salts and ester forming groups.

* * * * *